US008613710B2

(12) United States Patent
Kolanko et al.

(10) Patent No.: US 8,613,710 B2
(45) Date of Patent: Dec. 24, 2013

(54) NONINVASIVE METHOD FOR DETERMINING THE PRESENCE OF SYSTEMIC HYPERTENSION IN A SUBJECT

(76) Inventors: Christopher J. Kolanko, Morgantown, WV (US); Lance Molnar, Morgantown, WV (US); James V. Odom, Morgantown, WV (US); James E. Smith, Morgantown, WV (US)

( * ) Notice: Subject to any disclaimer, the term of this patent is extended or adjusted under 35 U.S.C. 154(b) by 1922 days.

(21) Appl. No.: 11/331,014

(22) Filed: Jan. 13, 2006

(65) Prior Publication Data
US 2006/0253002 A1    Nov. 9, 2006

Related U.S. Application Data

(60) Provisional application No. 60/643,616, filed on Jan. 13, 2005.

(51) Int. Cl.
*A61B 13/00*    (2006.01)
*A61B 3/00*    (2006.01)
*G06K 9/00*    (2006.01)

(52) U.S. Cl.
USPC ............ 600/558; 351/200; 382/117; 382/128

(58) Field of Classification Search
USPC ........... 600/558; 351/200; 396/118; 382/117, 382/128
See application file for complete search history.

(56) References Cited

U.S. PATENT DOCUMENTS

| | | | |
|---|---|---|---|
| 4,993,825 A | 2/1991 | Abe et al. | |
| 5,125,730 A | 6/1992 | Taylor et al. | |
| 5,778,893 A | 7/1998 | Potter | |
| 6,022,109 A | 2/2000 | Dal Santo | |
| 6,110,110 A * | 8/2000 | Dublin et al. | 600/405 |
| 6,162,186 A | 12/2000 | Scinto et al. | |
| 6,305,804 B1 | 10/2001 | Rice et al. | |
| 6,387,618 B1 | 5/2002 | Kolanko et al. | |
| 6,477,394 B2 | 11/2002 | Rice et al. | |
| 6,544,193 B2 | 4/2003 | Abreu | |
| 6,547,394 B2 | 4/2003 | Doherty | |
| 6,565,210 B2 | 5/2003 | Kobayashi et al. | |
| 6,626,537 B1 | 9/2003 | Odom et al. | |
| 6,631,989 B2 | 10/2003 | Odom et al. | |
| 6,637,885 B2 | 10/2003 | Petrali | |
| 7,703,918 B2 * | 4/2010 | Kolanko et al. | 351/205 |
| 2002/0171805 A1 * | 11/2002 | Odom et al. | 351/221 |

OTHER PUBLICATIONS

Schubert, "Ocular Manifestations of Systemic Hypertension", Current Opinion in Ophthalmology, 1998, 9; VI: 69-72.*
International Search Report for PCT/US03/41220 dated Oct. 5, 2004.
International Search Report and Written Opinion for PCT/US07/077739, dated Aug. 20, 2008.

* cited by examiner

Primary Examiner — Sean Dougherty
Assistant Examiner — Devin Henson
(74) Attorney, Agent, or Firm — Patton Boggs LLP

(57) ABSTRACT

A non-invasive method for determining and characterizing the presence of damage or abnormalities resulting from or concomitant with systemic hypertension in subject. This method is comprised of the acquisition of ocular image(s) and subsequent evaluation, classification and/or interpretation of these image(s). The ocular image(s) may be acquired by photography. Evaluation, classification, and/or interpretation may be automated or involve the active participation of a human. The ocular images may be classified into either a normal or clinical group or compared to an algorithm of hypertensive symptoms. The ocular images may, additionally, be processed and have the pertinent characteristics extracted to make the classification more exact.

20 Claims, 3 Drawing Sheets

NONINVASIVE METHOD FOR DETERMINING THE PRESENCE OF SYSTEMIC HYPERTENSION IN A SUBJECT

RELATED APPLICATIONS

This application claims priority to U.S. Provisional Application Ser. No. 60/643,616, filed Jan. 13, 2005, which is incorporated herein by reference in its entirety.

FIELD OF THE INVENTION

The present invention relates to a non-invasive method for determining hypertension in a patient by obtaining an ocular image and classifying the image characteristics. Classification may be accomplished by manual examination or by comparing the ocular characteristics to ocular characteristics in other individuals using an algorithm (or comparing to pre-existing/prior images from the same individual). The ocular images may be classified as normotensive or as varying degrees of hypertensive.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Systemic hypertension, or high blood pressure, is an extremely common disorder, affecting approximately 30% of adults aged 18 to 74. The vast majority of these cases (approximately 90%) are termed essential, or primary, hypertension due to an unknown etiology. Generally, individuals are diagnosed as having hypertension if they have an abnormally elevated blood pressure (systolic and/or diastolic) upon repeated visits to a clinician. Hypertension tends to increase mortality and shorten the life expectancy of those affected through its effects on major end organs, namely the heart and cardiovascular system, the kidneys, and the brain. Unfortunately, as with many other diseases which do not have outwardly obvious symptoms, only about one-half of those with the disease are aware of the condition.

The circulatory system is a closed system in which the pressure varies constantly. It rises to a peak (termed the systolic pressure) soon after the tightening (contraction) of the main pumping chambers of the heart (the ventricles). It then falls to a lower level (termed the diastolic pressure) just before the next heartbeat/contraction. Thus, the diastolic pressure is the running pressure between heartbeats. In essence, these pressures are determined by the volume of blood being pumped by the heart and the resistance of the peripheral vessels. The total peripheral resistance created by these vessels is, in turn, primarily dependent upon vessel diameter/size which is normally autoregulated to meet the needs of the organism.

Complications secondary to hypertension are numerous and represent many of the health risks associated with this disease. Arterial damage may lead to a decrease in the normal elasticity of these vessels (arteriosclerosis), inhibiting the ability of the arterioles to adjust/adapt to the changing cardiovascular needs of the individual. Persistent elevations in blood pressure also promote atherosclerosis, a narrowing of the arteries resulting from the development of fatty plaques in the intima of larger arteries. This narrowing can decrease the amount of blood flow, inhibiting oxygenation of the tissue. In addition, the increased blood pressure may cause the release of such plaques from the vessel walls leading to the development of occlusions within the circulatory system. These occlusions (or infarcts) cause small areas of hypoxia and cell death. If such occlusions occur in the brain, they may result in a stroke and possibly severe damage. Other common results of prolonged hypertension include cardiac hypertrophy (increased heart size) due to the increased pumping demands placed upon the heart, cardiac failure, renal/kidney failure, and, in extreme instances, blindness due to the rupturing of vessels within the eye.

In clinical medicine, it is common to classify (or stage) hypertension in terms of the pressure at the time of presentation. There are three primary difficulties with this strategy. First, a significant number of hypertensive patients are not reliably detected during the early stages of their disease. Secondly, given individual variability in the progression of hypertension, the severity of the patient's condition cannot be accurately determined based on the stage of hypertension alone. Therefore, the major means of analyzing the severity of the person's disease is to assess the effects of the hypertension on significant end organs (the heart and kidneys); typically through electrocardiograms and blood work. Finally, due to the typical lack of outwardly apparent symptoms of hypertension, individuals are less likely to visit a clinician. This factor becomes even more important among individuals who live in areas or environments, which do not promote regularly schedule health diagnostic visits.

In addition to the heart and kidneys, the eye is a major end organ affected in hypertensive patients. In addition, it is the only place in the body where the rich microvascular networks can be directly observed in a non-invasive manner. Evaluating the changes observed in these arteries and arterioles to discern changes which occur in other end organs and deciphering what immediate/pertinent health risks are present would help speed discovery of this dangerous condition. The present device analyzes and, subsequently, utilizes these changes for diagnostic evaluation.

Our investigations have shown that the ocular vessels change in several distinctive ways secondary to hypertension. We have observed four different grades of retinal vessel damage via an ophthalmoscopic examination:

We characterize the first grade as a generalized arteriolar narrowing. The characteristics comprise a more linear appearance of at least some of the arteries in the retina. We also find that the arteries reflect more light due to wall thickening. Finally, we can see greater variations in artery caliber (size). The second grade is a generalized arteriolar narrowing with focal constrictions. The characteristics comprise arteriovenous (A-V) nipping, e.g., veins may be compressed by crossing arteries. The third grade is an increased arteriolar narrowing, focal constrictions, and/or hemorrhage, and/or exudation with the characteristics further comprising flame shaped hemorrhages and/or soft white ("cotton wool") exudates (areas of retinal infarction). The forth grade is a further marked arteriolar narrowing, with focal constrictions, hemorrhage, exudation, and/or edema of the disc (papilloedema) and the characteristics further comprising visible swelling of the optic disc and in some cases lipid deposits within the eye.

The choroidal vessels are only viewed directly with difficulty. With the aid of dyes such as fluorescein and indocyanine green, however, they may be more easily functionally visualized. The choroid receives considerable sympathetic innervation. Therefore, vasoconstrictive factors (e.g., angiotensin IT, adrenaline, and vasopressin) and other factors related to sympathetic activity in the cardiovascular system are likely to affect the choroidal system earlier and/or more severely than the retinal vasculature. Using dye tests, one can observe both narrowing of the choroidal vessels and leakage of fluid from these vessels. The areas of leakage often appear to be yellowish in the fundus and are termed Elschnig's spots. A summary is presented below:

Narrowed choroidal vessels detectable using fluorescein
Elschnig's spots are observed following a choroidal infarct as an elongated yellowish spot
Siegrist's spots are observed following an infarct of the retinal pigment epithelium as circular spots along the equator/midline of the eye
Leakage of fluid from the vessels is visible through a variety of dye tests
Subretinal exudates are form by the accumulation of fluid from leakage and may be visualize
Retinal detachment may occur with increased fluid accumulation
Retinal pigment epithelium depigmentation (i.e., death of the retinal pigment epithelium) occurs following chronic focal ischemia The optic nerve contains the only true arteries in the eye. The arteries may develop atherosclerosis (vessel wall deposits), which is visible ophthalmoscopically. More commonly, however, one observes optic disc swelling or edema. After chronic edema one observes optic disc pallor and optic disc ischemia. The ischemic changes observed in the optic nerve may actually be secondary to changes in the choroid as much of the nourishment of the optic nerve comes from the choroid. Therefore, changes in the optic nerve often reflect rather late hypertensive changes.

The indirect association of eye findings with hypertension and cardiovascular disease has been established for some time. One may legitimately ask why this association is not exploited more vigorously in clinical medicine to evaluate and assist in classifying hypertensive patients and then directing and monitoring their subsequent therapy. There are at least four basic reasons. First, those physicians who are primarily trained in the care of hypertensive patients have little training in observing the ocular findings. Second, the ocular findings in hypertension are not threatening to vision (except in very advanced/critical need hypertensive patients) and, therefore, are of only moderate interest to physicians interested in treating eye disease. Third, normal clinical evaluation of the ocular signs is difficult. This is due to both normal individual variability and because some of the early changes in hypertension is also observed as the result of the normal aging process. Finally, once hypertension is discovered, simple blood pressure monitoring by well established methods such as a sphygmomanometer can be done routinely with little training.

Prime examples of the difficulties in interpreting ocular findings in hypertension are the changes in the artery size, shape and color. The arteries of normal subjects vary considerably and artery size changes with age. Moreover, the apparent size of the retinal vessels changes with refractive error and intraocular length. Therefore, without an individual adjustment for the eye's optics, absolute size estimates are too variable to be of use in a clinical context. A second example of the difficulty in using ocular display technology in cardiovascular research is the case of cotton wool spots. Cotton wool spots resolve in several months time and if the hypertension is treated, they disappear completely. In many of the places where cotton wool spots were present, however, there are dead ganglion cells, since the cause of the cotton wool spots are the accumulation of axoplasmic materials in hypoxic axons. Due to the lack of blood vessels in the central retina, this loss of visual cells is often unnoticed by the patient and therefore of little or no concern to the ophthalmologist. The pressure of residual nerve fiber layer defects, however, points to a more severe level of end organ damage and can be used as a marker for past periods of hypertension.

A need therefore exists for a non-invasive method for determining hypertension in a patient by obtaining ocular images.

SUMMARY OF THE INVENTION

The present invention comprises a relatively non-invasive method for determining damage or abnormalities in the eye (s) resulting from or concomitant with hypertension in a subject by acquiring ocular image(s) and classifying ocular characteristics present in these images to determine hypertensive status. The method has the advantage of allowing the non-invasive determination of hypertensive status.

In one embodiment, the present invention comprises a non-invasive method for diagnosing hypertension in a subject comprising: a) acquiring one or more ocular images; b) processing the ocular images; c) extracting one or more ocular characteristics from the ocular images; and d) classifying the ocular characteristics. In another embodiment, any of steps a) through d) listed above may be performed using an automated device. In a further embodiment, the ocular images are acquired using photography. Alternatively, the digital image can be electronically transmitted to a medical service provider or instrument for further analysis. In an additional embodiment, the ocular characteristics are classified as either normal or abnormal. In yet another embodiment, the method further comprises classifying the ocular characteristics into a clinical classification. In some embodiments, the clinical classification is selected from the group consisting of Normotensive, Pre-Hypertensive, Stage 1 Hyertensive and Stage 2 Hypertensive.

Embodiments of the present invention further provides a non-invasive method of determining the progression of hypertension in a subject comprising: a) acquiring, processing and extracting a first ocular characteristic according to the above described method; b) acquiring, processing and extracting a second ocular characteristic according to the above described method; and c) comparing the first ocular characteristic and the second ocular characteristic; wherein the first ocular characteristic and the second ocular characteristic are acquired, processed and extracted sequentially over time and wherein differences in the ocular characteristics indicate a change in the progression of hypertension in the subject. In one aspect, the method further comprises classifying the second ocular characteristic. In an additional aspect, any of steps a) through c) listed above may be performed using an automated device. In another aspect, the ocular images are acquired using photography. In still another aspect, the method further comprises classifying the second ocular characteristics into a clinical classification. In yet another aspect, the clinical classification is selected from the group consisting of Normotensive, Pre-Hypertensive, Stage 1 Hyertensive and Stage 2 Hypertensive.

Embodiments of the present invention further provide a non-invasive method of diagnosing hypertension in a subject comprising: a) acquiring, processing and extracting one or more ocular characteristics according to the above identified method; and b) comparing the ocular characteristics to a database of standard ocular characteristics obtained from a non-hypertensive population. Certain embodiments can then use the differences between the subject's ocular characteristic and the database of standard ocular characteristics to indicate an abnormality in the subject's ocular characteristics. In one embodiment, the method further comprises classifying the subject's ocular characteristics. In an additional embodiment, any of steps a) through b) listed above may be performed using an automated device. In yet another embodiment, the subject's ocular images are acquired using photography. In a further embodiment, the method further comprises classifying the ocular characteristics into a clinical classification. In still another embodiment, the clinical classification is selected from the group consisting of Normotensive, Pre-Hypertensive, Stage 1 Hyertensive and Stage 2 Hypertensive.

DETAILED DESCRIPTION OF THE INVENTION

Figure 1:
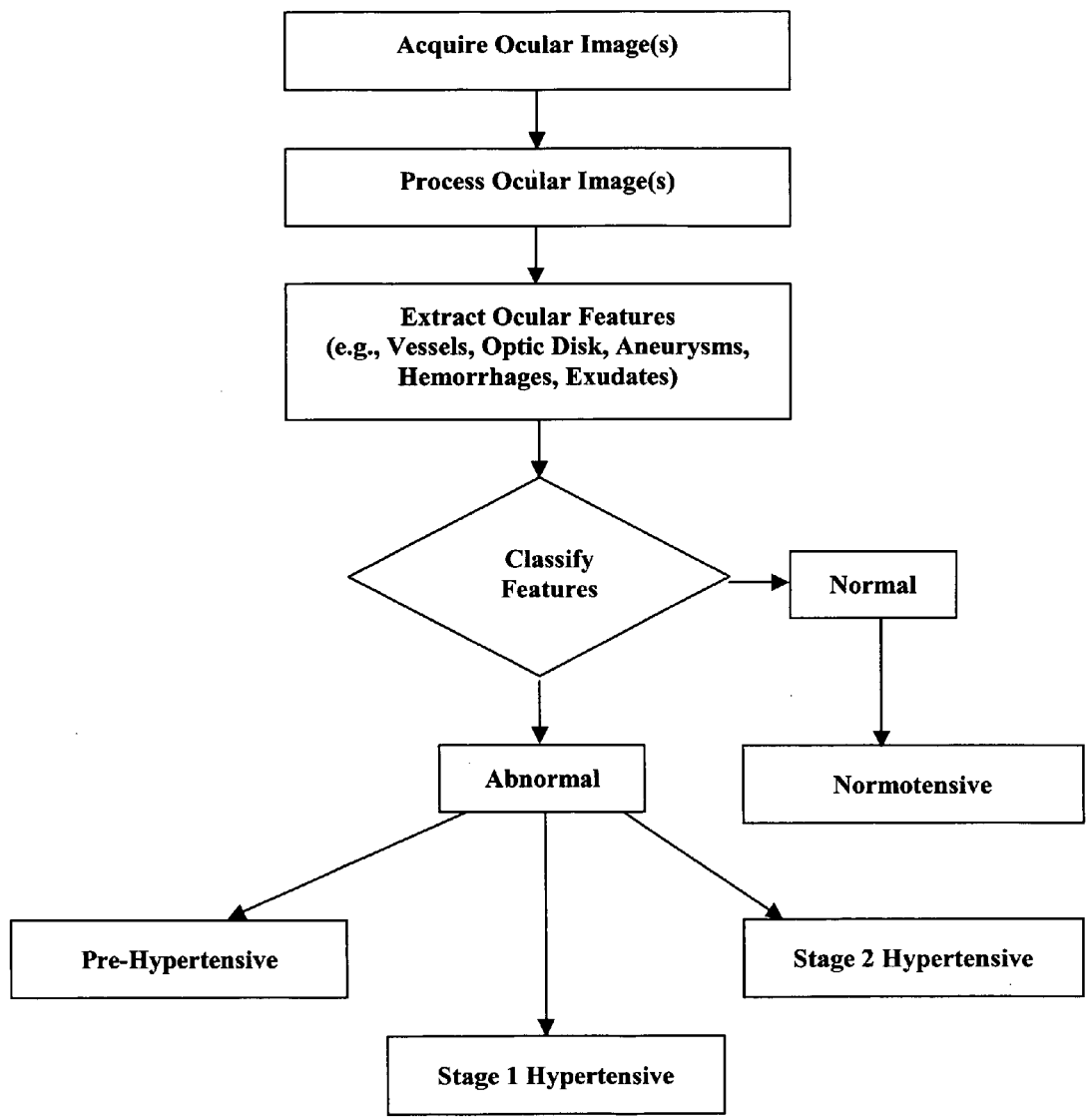
FIG. 1 is a schematic view of the steps in the method for determining hypertension in a patient.

An embodiment of the present invention is described in detail in the following.

As used herein, the term "subject" refers to human beings and other members of the animal kingdom unless in a specific usage and express indication to the contrary is provided.

The term "hypertensive state" is intended to encompass a condition in which there exists in a subject a persistently or temporary raised mean arterial pressure, diastolic pressure, and/or systolic blood pressure.

An "ocular characteristic" is a measurable physical attribute determined via the observation of external or internal features of the eye(s). Non-limiting examples of an ocular characteristic important to the diagnosis of hypertension include blood vessel architecture color and reflectance, ischemic spots, nerve fiber layer loss, choroidal infarcts, Eischnig's spots exudates and hemorrhages. An altered ocular characteristic can be the result of a hypertensive state.

The present invention relates to a method of diagnosing and classifying hypertension in a subject. The method of diagnosing the hypertensive state preferably includes, in general, the steps of: 1) examining the subject's eye(s) to determine whether the subject exhibits an ocular characteristic indicative of hypertension, and if so 2) evaluating any ocular characteristic in to further classify the hypertensive state, including the severity. One or more altered ocular characteristics can indicate the existence of a hypertensive condition in a subject.

The non-invasive methods of the present invention for determining hypertension in a subject utilize changes in the eye, for example, changes in ocular features to determine the presence and/or magnitude of end organ damage in patients suffering from systemic hypertension. The eye is a privileged end organ affected by hypertension and is the only place in the body where microvascular networks can be directly observed. Changes in the vessels, arteries and arterioles of the eye correspond with changes ongoing in other end organs.

An initial step in the methods of the invention involves acquiring an image of the eye, e.g. an image of the retina, optic nerve, choroids and/or pupil. Multiple images, types of images and regions of the eye may be examined. In one embodiment of the invention, images acquired from one eye of the patient may be sufficient. In an additional embodiment, images from both eyes may be used.

A subject's eye(s) can be examined using various means commercially available and known to those skilled in the art. In a presently preferred embodiment, a subject's eyes are examined, for example, through the use of a blood flow meter, nerve fiber analyzer and/or standard fundoscope, all of which are well know in the art. The images can be acquired by photography, the use of an automated device, a computer, or other imaging equipment. A monocular or binocular device (capable of imaging both eyes simultaneously) may be used in the methods of the present invention to capture the ocular images.

In one embodiment of the present invention, the subject's eyes are examined passively, where the Examiner may manipulate the eyes to obtain an ocular image but the subject is not required to voluntarily act or react to external stimuli. The subject's eyes are evaluated using one or more ocular characteristics (for example, arteriolar width, focal constrictions, hemorrhages, exudates, cotton wool spots, etc.). By analyzing these ocular characteristics, a diagnosis may be made either manually by a caregiver, or automatically, i.e., without the need for manual measurement, analysis or diagnosis, by a processing unit or similar means employing a decision tree or algorithm.

In another embodiment, ocular characteristics of a subject's eye are evaluated by first quantifying the ocular characteristic under consideration. For example, the vasculature of the subject's eye can be measured and assigned a numerical character corresponding to size, length, diameter, branching characteristics, etc. This number, or quality, can be compared easily to a normal eye under similar conditions, which also has been quantified by assigning an appropriate numerical character. The norm for the ocular characteristic (size, length, diameter, color, reflectance, etc.) preferably is established for each subject being examined. However, average normal values can be established for different population and subpopulations. A subject's quantified ocular data can then either be compared to his or her personal normal value, or it can be compared to an average value established for a population to which the subject belongs (e.g., FIGS. 2 and 3). In doing so, a person examining a subject's eye can determine if one or more ocular characteristics indicate a hypertensive state.

As described previously, ocular blood vessels, including retinal arteries and veins, can be examined using various means known to those skilled in the art, such as a fundoscope. An optics system may then be employed for creating an image of the subject's eye. This can be done, for example, by altering shutter mechanics or adjusting mounting to allow a camera to be attached, etc. Alternatively, a commercially available digital findoscope may be used. Additional methods used to image the eye may include mydriatic or nonrnydriatic fundus cameras, scanning laser ophthalmoscopy, with or without the use of injectable dyes and indocyanine green angiography.

The methods of the present invention may be used in conjunction with a "dye" or other chemical injected into the blood stream or applied to the surface of the eye or its surrounding tissues. The changes in the eye caused by the dye could provide indications of the health of the vasculature and tissues. Examples of this include, but are not limited to, current uses of fluorescein or other chemicals applied to the surface of the eye or orbit or injected to reveal vessels of the eye, retina, pupil and other ocular tissues. The externally visible portions of the eye and its surrounding tissues or features within the eye may then be monitored using the methods of the invention.

In one embodiment, the current invention utilizes an ocular technology (Ocular Scanning Instrumentation, OSI) developed by MD Biotech, Morgantown, W.V. The OSI technology employs non-invasive imaging of ocular characteristics. The instrumentation is capable of evaluating, analyzing and quantifying several ocular characteristics such as pupil size and motility (light reflexes), corneal abnormalities (clouding, blistering and ulcerations) and blood coloration/oxygentation (including arterial and vein discrimination). Any instrument with the capability to determine morphology, structure and other damage indicators would be appropriate to carry out the methods of the invention. The OSI instrumentation operates in several steps. The first step comprises pre-processing of the image. This includes color normalization and spatial filtering. The second step is object identification. Here, the optic disc (optic nerve head) or fovea is identified. The third step consists of blood vessel tracking, identification and analysis, where the vessels are detected and observed. Finally, the fourth step consists of identification of abnormalities and exudates.

After acquiring an ocular image, the image can be processed using techniques of film processing, a computer program or automated device. The processing step is followed by the extraction of the ocular features from the rest of the ocular image. This extraction can be performed on the device used for processing the ocular image or may utilize a separate computer program or automated device.

A trained clinician may perform analysis of the resulting ocular images manually. Analysis may be based upon the ocular clinical hallmarks or pathology of hypertension, such traits including vessel crossovers, vessel tortuosity (bending), and evidence of exudates as these are the most likely early indicators of the disease state. The images are carefully analyzed to determine the hypertensive status and markers of end organ damage in patients.

In a preferred embodiment, the ocular images may be analyzed via an automated method through the use of algorithms on a computer subsequent to uploading. The automated methods of the invention will use algorithms utilizing multiple image process techniques for analyzing the images generated by these systems. The algorithms will relate the appearance and extent of vessel changes and other abnormalities to hypertensive state and end organ damage.

The algorithms may be capable of, in an automated fashion, searching for blood vessel alterations and other abnormalities in the ocular images. The algorithms may match the capabilities of manual analytical methods (scoring and analysis). Suitable computer algorithms may have the ability to: (1) accurately and sensitively identify the existence of ocular abnormalities; (2) accurately specify the type and extent of such abnormalities; and (3) correlate such findings to the hypertensive state of an individual. The automated method may provide a much more advanced capability for abnormality detection. Through automated processing techniques and the removal of qualitative evaluation, greater information may be derivable from the images. Advantages of the preferred embodiments of the present invention include increased vessel diameter measurement accuracy, enhanced statistical evaluation of vessel tortuosity, and more sensitive discrimination of exudate and abnormality occurrence.

The methods of the invention also include the classification of the ocular features. The classification comprises different ways to group or stage the ocular image as either diseased or healthy. The classification may comprise placing the ocular image into a classification of groups based upon average diastolic and systolic blood pressure. In one embodiment, as illustrated in Table 1, the stages of hypertension may be classified into four categories comprising normal (normotensive), pre-hypertension, stage 1 hypertension and stage 2 hypertension. Alternatively the classification may comprise comparing the ocular image to an algorithm of disease symptoms. The algorithm of disease symptoms comprises ocular hypertensive changes: changes in size, changes in shape, changes in color, hemorrhages, cotton wool spots, leakage, hard exudates, and edema. Pupillary and chorodial vessels may also show disease symptoms especially when a dye is used. The choroidal vessel hypertensive symptoms comprise: narrowed choroidal vessels, Elschnig's spots, Siegrist's spots, leakage, subretinal exudates, serous retinal detachments, retinal pigment epithelium depigmentation, and choroidal sclerosis. Optic nerve vessels reflect changes in the optic nerve due to hypertension.

TABLE 1

Staging of Hypertension.

| Average DBP (mmHg) | Average SBP (mmHg) | | | |
|---|---|---|---|---|
| | Less than 120 | 120-139 | 140-159 | 160 and higher |
| Less than 80 | Normal | Pre-hypertension | Stage 1 hypertension | Stage 2 hypertension |
| 80-89 | Pre-hypertension | Pre-hypertension | Stage 1 hypertension | Stage 2 hypertension |
| 90-99 | Stage 1 hypertension | Stage 1 hypertension | Stage 1 hypertension | Stage 2 hypertension |
| 100 and higher | Stage 2 hypertension | Stage 2 hypertension | Stage 2 hypertension | Stage 2 hypertension |

In a preferred embodiment, the automated methods of the invention comprise algorithms utilizing multiple image process techniques for analyzing the images generated by these systems. The images may then be carefully analyzed to determine the hypertensive status and markers of end organ damage in patients. Finally, the findings may then be statistically correlated with other criteria to classify the patient.

In one embodiment of the present invention, the clinician will study the ocular images or examine the automated ocular analysis and make a determination as to hypertensive state. This method is illustrated in FIG. 1. Here, the methods of the invention are used to classify systemic hypertension in a patient. In the first step of the method involves acquisition of the patient's ocular image. The second step involves processing of the ocular image. Next, the ocular images are extracted and the features classified. The classification is based upon established criteria of ocular abnormalities and damage. Trained personnel may perform the extraction and classification steps manually. In an additional embodiment of the present invention, the extraction and classification steps may be based upon algorithmic quantification and interpretation. The features are then grouped as "abnormal" or "normal" based upon the outcome of the classifications steps. Abnormal features may be further classified based upon their clinical presentation (i.e., normotensive, pre-hypertensive, stage 1 hypertensive or stage 2 hypertensive).

Figure 3:
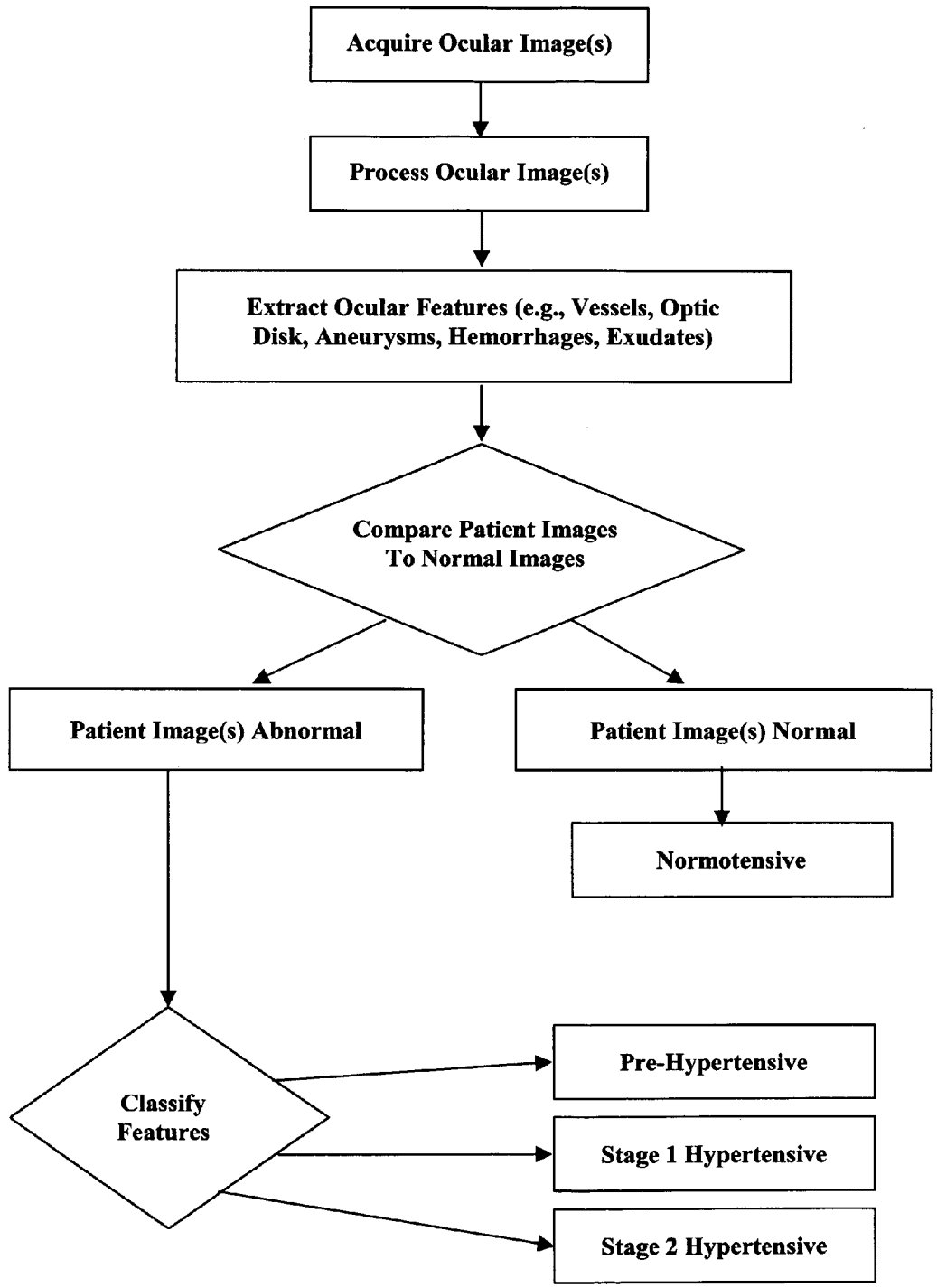
FIG. 3 is a schematic view of the steps in the method for determining hypertension in a patient when compared to a nonhypertensive patient.

In an additional embodiment, the ocular images may be compared to standard photographs in a collected database, as illustrated in FIG. 3. This database may include, but is not limited to, color images of (1) the posterior pole, centered on the macula, (2) looking up, down, left and right with approximately 30 degrees of deviation from center for each, (3) stereo photographs of the optic disk/nerve head (2 photographs at 15 degrees offset), and (4) a red free photograph of the posterior pole. The images in the database represent "normal" ocular features, i.e., those obtained from a non-hypertensive population. The subject's acquired image(s) are classified as either abnormal or normal based upon comparison to quantifiable criteria obtained from a normal sample as contained in the database. Patients with abnormal images may be identified for further evaluation. In addition, the patient's hypertensive status may be re-classified based upon this comparison (i.e., normotensive, pre-hypertensive, stage 1 hypertensive or stage 2 hypertensive).

Figure 2:
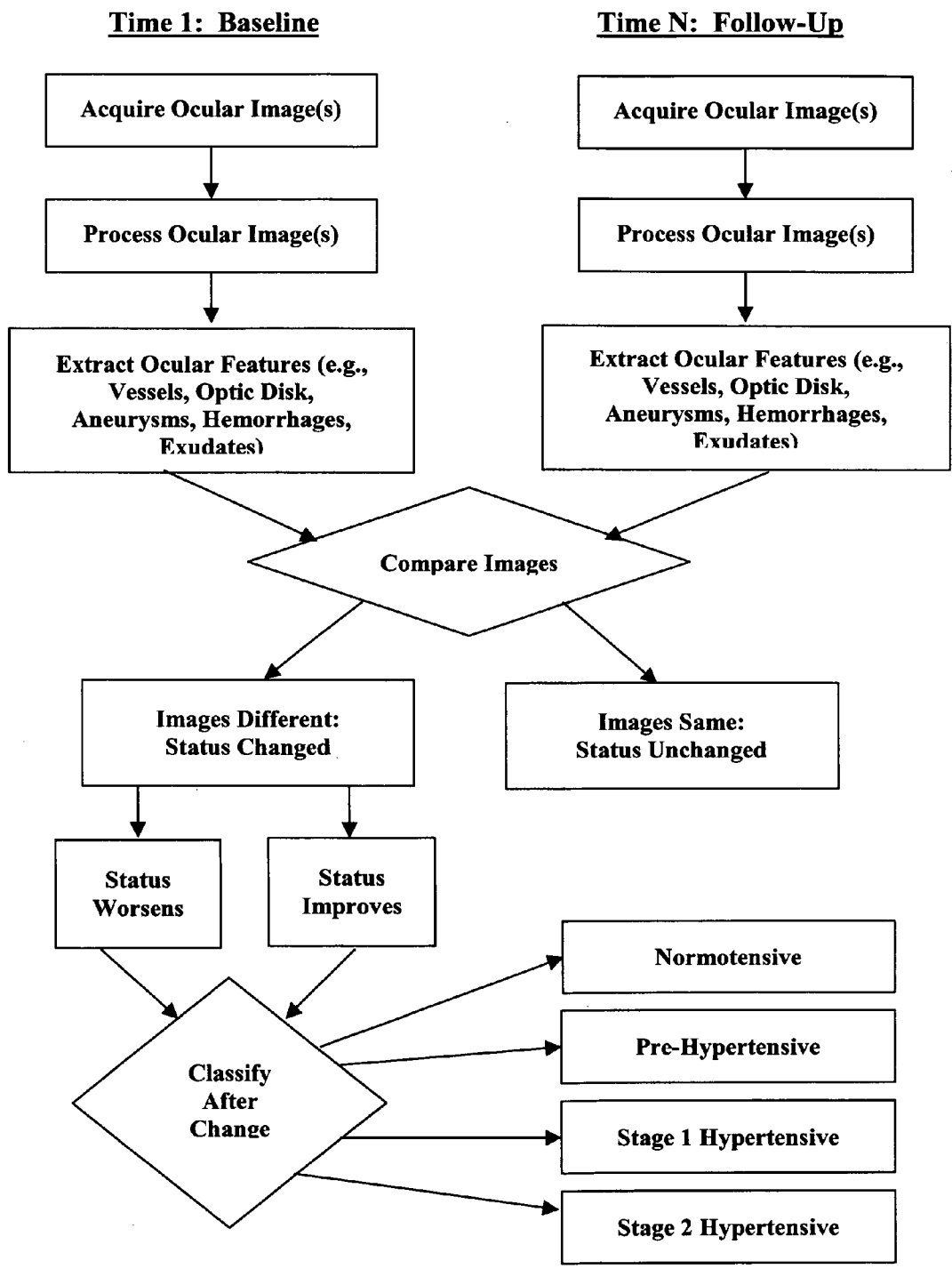
FIG. 2 is a schematic view of the steps in the method for determining progression of hypertension in an individual patient.

It will be appreciated that the invention may also be employed advantageously to provide for periodic monitoring of patients at intervals of days, weeks, months or years for comparison purposes to determine if meaningful changes have occurred over time. This embodiment of the invention is illustrated in FIG. 2. This figure illustrates steps in a method for determining the progression (or regression) of hypertension in a patient. To determine whether there has been significant change in an ocular characteristic, a baseline, or initial reading is first established for the characteristic. The initial characterization is preferably established for each subject using, for example, fundoscope or other imaging device for the internal regions of the eye. Alternatively, an average (or baseline) ocular characteristic reading for a given population to which the subject belongs can be obtained for comparison purposes. In this embodiment, the patient's ocular features are classified on a first visit as either diseased or healthy and then subsequent follow-ups allow the monitoring of change in the ocular features. Based upon the initial or previous classification and analysis of ocular features, subsequent employment of the current method could be used to monitor progression or regression of hypertensive status based upon stasis, worsening, or improvement of ocular abnormalities resulting from or concomitant with hypertension. This aspect of the method would serve to evaluate (1) the efficacy of any hypertensive therapies initiated since previous ocular analysis, (2) patient compliance with initiated therapies, and/or (3) the need for alternative or additional hypertensive therapies. Abnormal features may be re-classified based upon their changed clinical presentation (i.e., normotensive, pre-hypertensive, stage 1 hypertensive or stage 2 hypertensive).

Despite the difficulties in evaluation ocular signs in hypertension, the present invention offers improvement for the utility of ocular signs in the evaluation of hypertension and subsequent therapeutic intervention. First, the last decade has seen the development of several new and more powerful strategies and techniques for examination of the eye. Second, as technology has advanced and become far more cost effective, the feasibility of developing automated algorithms for evaluating these ocular findings has emerged. Third, through automation, the concurrent evaluation and interpretation of multiple ocular characteristics may be more thoroughly and efficiently combined to provide increased diagnostic capability and reliability without the need for specialized training. Finally, via an automated technique of quantitative and statistical evaluation of ocular characteristics more precise and accurate alterations may be identifiable which will aid in pathology recognition, allow more thorough examination of potential changes, and subsequently provide increased diagnostic capabilities through ocular evaluation.

It is to be understood that the present invention is not limited to the embodiments described above, but encompasses any and all embodiments within the scope of the following claims.

What is claimed is:

1. A non-invasive method for diagnosing hypertension in a subject, the method comprising:
   a) acquiring one or more ocular images;
   b) processing said ocular images;
   c) extracting one or more ocular characteristics from said ocular images; and
   d) classifying, by a processor, said ocular characteristics, wherein the classifying comprises:
      measuring said ocular characteristics;
      assigning a numerical character corresponding to markers of end organ damage from said measured ocular characteristics;
      comparing the numerical character to a normal numerical character based on a normal eye under similar conditions;
      converting the comparison of the numerical character corresponding to the markers of end organ damage from said measured ocular characteristics and the normal numerical character based on a normal eye under similar conditions to a classification of average diastolic and systolic blood pressure;
      indicating a presence or absence of a hypertensive state; and
      if a hypertensive state exists, indicating a severity of the hypertensive state by grouping based on average diastolic and systolic blood pressure.

2. The method of claim 1, wherein the processing further comprises:
   pre-processing of said ocular image;
   identifying ocular characteristics;
   tracking, identifying and analyzing blood vessels; and
   identifying abnormalities and exudates.

3. The method of claim 1, wherein the one or more ocular images are from one eye of the patient.

4. The method of claim 1, wherein the ocular characteristics are selected from the group consisting of: blood vessel architecture color and reflectance, ischemic spots, nerve fiber layer loss, choroidal infarcts, Eischnig's spots exudates, hemorrhages, and combinations thereof.

5. The method of claim 1, wherein the ocular characteristics are selected from the group consisting of: vessel crossovers, vessel tortuosity, evidence of exudates, and combinations thereof.

6. The method of claim 1, wherein the markers of end organ damage from said ocular characteristics are selected from the group consisting of:
   size, length, diameter, branching characteristics, color, reflectance, and combinations thereof.

7. The method of claim 1, wherein the classifying further comprises employing a decision tree or algorithm.

8. A non-invasive method of determining the progression of hypertension in a subject comprising:
   acquiring one or more first ocular images;
   processing said first ocular images;
   extracting a first ocular characteristic from said first ocular images;
   acquiring one or more second ocular images;
   processing said second ocular images;
   extracting a second ocular characteristic from said second ocular images;
   assigning a numerical character corresponding to markers of end organ damage from said first ocular characteristic;
   assigning a numerical character corresponding to markers of end organ damage from said second ocular characteristic;
   comparing the numerical character corresponding to the markers of end organ damage from said first ocular characteristic and the numerical character corresponding to the markers of end organ damage from said second ocular characteristic;

converting, by a processor, the comparison of the numerical character corresponding to the markers of end organ damage from said first ocular characteristic and the numerical character corresponding to the markers of end organ damage from said second ocular characteristic into a classification of average diastolic and systolic blood pressure, wherein the first ocular characteristic and the second ocular characteristic are acquired, processed and extracted sequentially over time and wherein differences in the ocular characteristics indicate the relative change in hypertension status in said subject, and if a hypertensive state exists, indicating a severity of the hypertensive state by grouping based on average diastolic and systolic blood pressure.

9. The method of claim 8, further comprising re-classifying hypertension status in said subject based on differences from the first ocular characteristic to the second ocular characteristic.

10. The method of claim 8, wherein the one or more ocular images are from one eye of the patient.

11. The method of claim 8, wherein the ocular characteristics are selected from the group consisting of: blood vessel architecture color and reflectance, ischemic spots, nerve fiber layer loss, choroidal infarcts, Eischnig's spots exudates, hemorrhages, and combinations thereof.

12. The method of claim 8, wherein the ocular characteristics are selected from the group consisting of: vessel crossovers, vessel tortuosity, evidence of exudates, and combinations thereof.

13. The method of claim 8, wherein the markers of end organ damage from said ocular characteristics are selected from the group consisting of:
size, length, diameter, branching characteristics, color, reflectance, and combinations thereof.

14. The method of claim 8, wherein the classifying further comprises employing a decision tree or algorithm.

15. A non-invasive method of determining the progression of hypertension in a subject comprising:
acquiring one or more first ocular images;
processing said first ocular images;
extracting a first ocular characteristic from said first ocular images;
assigning a numerical character corresponding to markers of end organ damage from said first ocular characteristic; and
comparing the numerical character corresponding to the markers of end organ damage from said first ocular characteristic to a database of numerical characters corresponding to standard ocular characteristics obtained from a non-hypertensive population,
converting, by a processor, the comparison of the numerical character corresponding to the markers of end organ damage from said first ocular characteristic and the database of numerical characters corresponding to standard ocular characteristics obtained from a non-hypertensive population into a classification of average diastolic and systolic blood pressure,
wherein differences between the numerical character corresponding to the markers of end organ damage from said first ocular characteristic to a database of numerical characters corresponding to standard ocular characteristics indicates a presence or absence of a hypertensive state, and
if a hypertensive state exists, indicating a severity of the hypertensive state by grouping based on average diastolic and systolic blood pressure.

16. The method of claim 15, wherein the one or more ocular images are from one eye of the patient.

17. The method of claim 15, wherein the ocular characteristics are selected from the group consisting of: blood vessel architecture color and reflectance, ischemic spots, nerve fiber layer loss, choroidal infarcts, Eischnig's spots exudates, hemorrhages, and combinations thereof.

18. The method of claim 15, wherein the ocular characteristics are selected from the group consisting of: vessel crossovers, vessel tortuosity, evidence of exudates, and combinations thereof.

19. The method of claim 15, wherein the markers of end organ damage from said ocular characteristics are selected from the group consisting of: size, length, diameter, branching characteristics, color, reflectance, and combinations thereof.

20. The method of claim 15, wherein the classifying further comprises employing a decision tree or algorithm.

* * * * *